US012778478B2

(12) United States Patent
Yoon et al.

(10) Patent No.: US 12,778,478 B2
(45) Date of Patent: Nov. 3, 2026

(54) CARDIAC MONITOR DEVICE

(71) Applicant: Medtronic, Inc., Minneapolis, MN (US)

(72) Inventors: Hyun J. Yoon, Vadnais Heights, MN (US); Eric B. Kalmes, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 53 days.

(21) Appl. No.: 18/868,279

(22) PCT Filed: May 10, 2023

(86) PCT No.: PCT/IB2023/054829
§ 371 (c)(1),
(2) Date: Nov. 22, 2024

(87) PCT Pub. No.: WO2023/233223
PCT Pub. Date: Dec. 7, 2023

(65) Prior Publication Data

US 2025/0325213 A1 Oct. 23, 2025

Related U.S. Application Data

(60) Provisional application No. 63/365,601, filed on May 31, 2022.

(51) Int. Cl.
*A61B 5/29* (2021.01)
*A61B 5/00* (2006.01)
(Continued)

(52) U.S. Cl.
CPC .............. *A61B 5/29* (2021.01); *A61B 5/0006* (2013.01); *A61B 5/263* (2021.01); *A61B 5/287* (2021.01);
(Continued)

(58) Field of Classification Search
CPC ....... A61B 5/263; A61B 5/287; A61B 5/3756; A61B 5/3705; A61B 5/0031; A61K 9/0024; A61K 31/65; A61K 31/496
See application file for complete search history.

(56) References Cited

U.S. PATENT DOCUMENTS 5,507,807 A * 4/1996 Shippert ............... A61M 31/00 604/59
8,086,313 B2 12/2011 Singhal et al.
(Continued)

FOREIGN PATENT DOCUMENTS

WO 2020123503 A1 6/2020
WO 2020226646 A1 11/2020

OTHER PUBLICATIONS

International Preliminary Report on Patentability from International Application No. PCT/IB2023/054829 dated Nov. 7, 2024, 8 pp.
(Continued)

*Primary Examiner* — Eun Hwa Kim
(74) *Attorney, Agent, or Firm* — Shumaker & Sieffert, P.A.

(57) ABSTRACT

An example implantable medical device includes a housing configured to house control circuitry that is configured to control functioning of the implantable medical device, an electrode positioned on an outer surface of the housing and connected to the control circuitry. The control circuitry is configured to monitor a physiological parameter of a patient via the electrode. The implantable medical device also includes an absorbable antibacterial layer disposed on the housing. The implantable medical device including the absorbable antibacterial layer is configured to be received within an implantation tool and delivered out of the implantation tool and into a patient.

19 Claims, 9 Drawing Sheets

(51) Int. Cl.

| | |
|---|---|
| ***A61B 5/263*** | (2021.01) |
| ***A61B 5/287*** | (2021.01) |
| ***A61B 5/318*** | (2021.01) |
| ***A61K 9/00*** | (2006.01) |
| ***A61K 31/496*** | (2006.01) |
| ***A61K 31/65*** | (2006.01) |

(52) U.S. Cl.

CPC ............ *A61B 5/318* (2021.01); *A61K 9/0024* (2013.01); *A61K 31/496* (2013.01); *A61K 31/65* (2013.01)

(56) References Cited

U.S. PATENT DOCUMENTS

| | | | | |
|---|---|---|---|---|
| 8,691,258 | B2 | 4/2014 | Heruth et al. | |
| 9,107,903 | B2 | 8/2015 | Nabutovsky et al. | |
| 10,556,114 | B2 | 2/2020 | Hafiz et al. | |
| 2007/0016089 | A1* | 1/2007 | Fischell | A61B 5/0031 600/521 |
| 2007/0093894 | A1 | 4/2007 | Darouiche | |
| 2012/0185004 | A1* | 7/2012 | McJames | A61L 31/08 607/3 |
| 2018/0043064 | A1 | 2/2018 | Wulfman et al. | |
| 2018/0193537 | A1 | 7/2018 | Honglei et al. | |
| 2019/0030218 | A1* | 1/2019 | Pulapura | A61L 31/146 |
| 2021/0212586 | A1 | 7/2021 | Iyer et al. | |
| 2021/0267634 | A1 | 9/2021 | Vanderpool et al. | |
| 2021/0343017 | A1 | 11/2021 | Jordan | |

OTHER PUBLICATIONS

International Search Report and Written Opinion of International Application No. PCT/IB2023/054829 dated Aug. 4, 2023, 11 pp.

* cited by examiner

CARDIAC MONITOR DEVICE

This application is a U.S. National Stage entry under 35 U.S.C. § 371 of International Application No. PCT/IB2023/054829, filed May 10, 2023, which claims priority from and the benefit of U.S. Provisional Application No. 63/365,601, filed on May 31, 2022, the entire content of each of which is incorporated herein by reference.

TECHNICAL FIELD

The disclosure relates to implantable medical devices.

BACKGROUND

Various implantable medical devices (IMDs) have been clinically implanted or proposed for therapeutically treating or monitoring one or more physiological and/or neurological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, implantable loop recorders, and pressure sensors, among others. Such devices may be associated with leads that position electrodes or sensors at a desired location or may be leadless with electrodes integrated into the device housing. These devices may have the ability to wirelessly transmit data either to another device implanted in the patient or to another instrument located externally of the patient, or both.

Although implantation of some devices requires a surgical procedure (e.g., pacemakers, defibrillators, etc.), other devices may be small enough to be delivered and placed at an intended implant location in a relatively noninvasive manner, such as by a percutaneous delivery catheter, transvenously, or using a subcutaneous delivery tool. As one example, subcutaneously implantable monitors have been proposed and used to monitor heart rate and rhythm, as well as other physiological parameters, such as patient posture and activity level. Such direct in vivo measurement of physiological parameters may provide significant information for clinicians to facilitate diagnostic and therapeutic decisions.

SUMMARY

The disclosure describes implantable medical devices including an absorbable antibacterial material, and associated techniques, structures, and assemblies configured to provide reduce, prevent, and/or eliminate infection related to medical devices that have been implanted within a patient. An implantable medical device (IMD) may include an absorbable antibacterial layer disposed on a portion of the housing of the device. The absorbable antibacterial layer may be applied on an outer surface of the housing and configured to reduce, prevent, and/or eliminate infection and/or migration of the IMD. The absorbable antibacterial layer may be configured to be compatible with an implantation tool configured to implant the IMD which may provide improved implantation of the IMD and improved sensing performance and reliability. The absorbable antibacterial layer may be configured to be compatible with an implantation tool configured to implant the IMD and absorbable antibacterial layer within a patient.

In one example, this disclosure describes an implantable medical device including: a housing configured to house control circuitry, wherein the control circuitry is configured to control functioning of the implantable medical device; an electrode positioned on an outer surface of the housing and connected to the control circuitry, wherein the control circuitry is configured to monitor a physiological parameter of a patient via the electrode; and an absorbable antibacterial layer disposed on the housing, wherein the implantable medical device including the absorbable antibacterial layer is configured to be received within an implantation tool and delivered out of the implantation tool and into a patient.

In another example, this disclosure describes a system including: an implantable medical device; and an implantation tool including: a tool body defining a longitudinal axis and a channel extending along the longitudinal axis, the channel having a distal opening, wherein the tool body is configured to receive the medical device within the channel; and a plunger slidably fitting within the channel and movable within the channel towards the distal opening, wherein a distal end of the plunger is configured to push a proximal end of the medical device out of the channel through the distal opening, wherein the absorbable antibacterial layer, when disposed on the housing of the implantable medical device, is configured to be compatible with the implantation tool.

In another example, this disclosure describes a kit including: an implantable medical device and an implantation tool including: a tool body defining a longitudinal axis and a channel extending along the longitudinal axis, the channel having a distal opening, wherein the tool body is configured to receive the medical device within the channel; and a plunger slidably fitting within the channel and movable within the channel towards the distal opening, wherein a distal end of the plunger is configured to push a proximal end of the medical device out of the channel through the distal opening, wherein the absorbable antibacterial layer, when disposed on the housing of the implantable medical device, is configured to be compatible with the implantation tool.

In another example, this disclosure describes an article including: a material layer having a first thickness; and an absorbable antibacterial material at least one of disposed on the material layer or disposed within the material layer, the absorbable antibacterial material configured to be absorbed by a patient from the material layer when the article is implanted within the patient, wherein the material layer is configured to be disposed on a housing of an implantable medical device, wherein the material layer, when disposed on the housing, is configured to be compatible with an implantation tool.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below. Other features, objects, and advantages will be apparent from the description, drawings, and claims.

BRIEF DESCRIPTION OF THE FIGURES

The details of one or more examples of this disclosure are set forth in the accompanying drawings and the description below. Other features, objects, and advantages of this disclosure will be apparent from the description, drawings, and claims.

Figure 1:
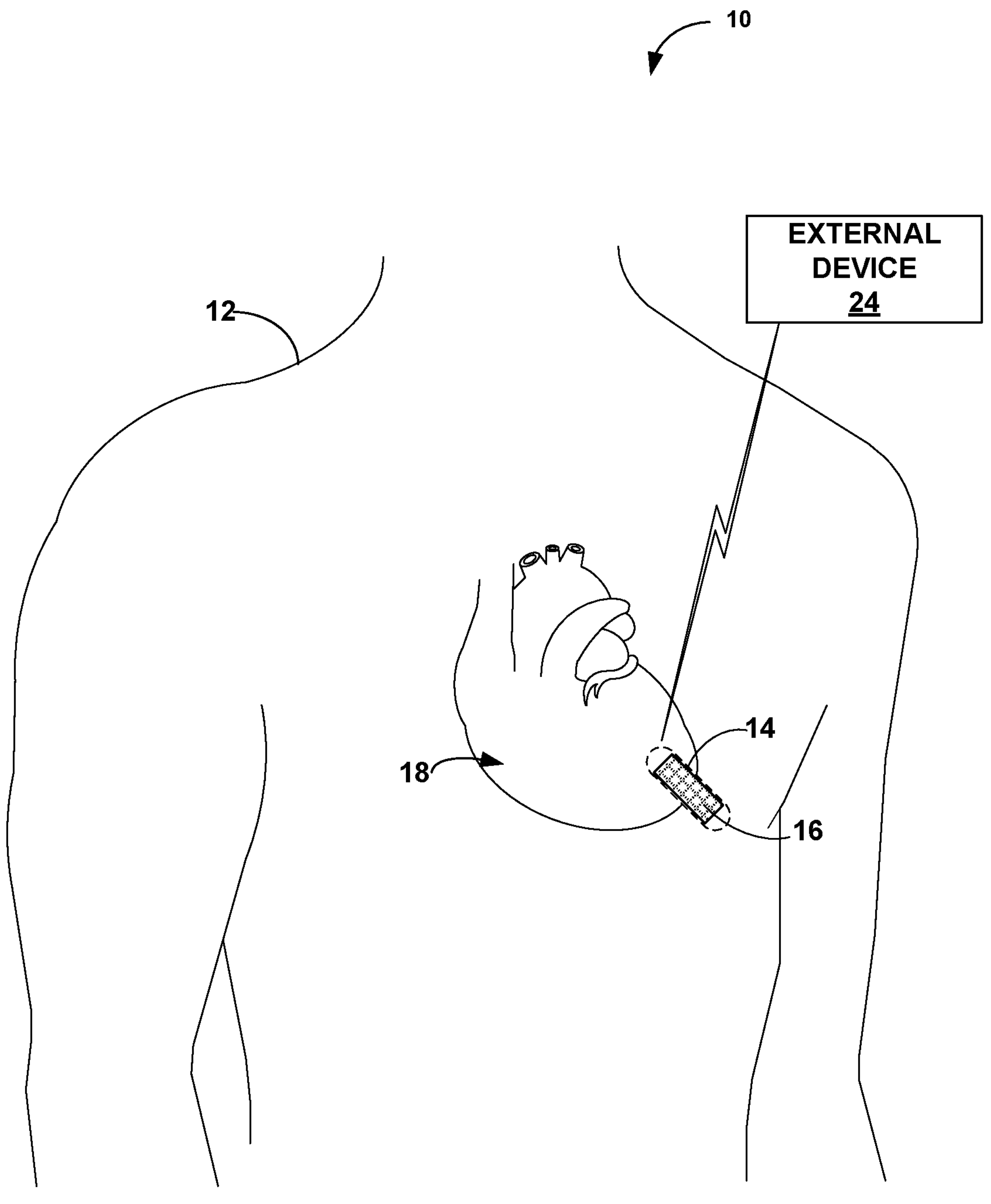
FIG. 1 is a conceptual drawing illustrating an example medical device system in conjunction with a patient, according to various examples described in this disclosure.

In the figures, use of a same reference number or a same reference number with a letter extension may be used to indicate a same or corresponding device or element when used in a same drawing or in different drawings. In addition, unless otherwise indicated, devices and/or other objects such as a patient, an implantable medical device, or an electrical device such as an electrical coil, are not necessarily illustrated to scale relative to each other and/or relative to an actual example of the item being illustrated. In particular, various drawings provided with this disclosure illustrate a "patient" represented by a human-shaped outline and are not to be considered drawn to scale relative to an actual human patient or with respect to other objects illustrated in the same figure unless otherwise specifically indicated in the figure for example by dimensional indicators, or for example as otherwise described in the text of the disclosure.

DETAILED DESCRIPTION

A variety of types of medical devices sense cardiac electrograms (EGMs) and/or other physiological signals or parameters of a patient. Some medical devices that sense cardiac EGMs and/or other patient signals or parameters are non-invasive, e.g., using a plurality of electrodes placed in contact with external portions of the patient, such as at various locations on the skin of the patient to sense cardiac EGMs. The electrodes used to monitor the cardiac EGM in these non-invasive processes may be attached to the patient using an adhesive, strap, belt, or vest, as examples, and electrically coupled to a monitoring device, such as an electrocardiogramar monitor, or other electronic device. The electrodes are configured to sense electrical signals associated with the electrical activity of the heart or other cardiac tissue of the patient, and to provide these sensed electrical signals to the electronic device for further processing and/or display of the electrical signals. The non-invasive devices and methods may be utilized on a temporary basis, for example to monitor a patient during a clinical visit, such as during a doctor's appointment, or for example for a predetermined period of time, for example for one day (twenty-four hours), or for a period of several days.

External devices that may be used to non-invasively sense and monitor cardiac EGMs include wearable devices with electrodes configured to contact the skin of the patient, such as patches, watches, or necklaces. One example of a wearable physiological monitor configured to sense a cardiac EGM is the SEEQ™ Mobile Cardiac Telemetry System, available from Medtronic plc, of Dublin, Ireland. Such external devices may facilitate relatively longer-term monitoring of patients during normal daily activities and may periodically transmit collected data to a network service, such as the Medtronic Carelink™ Network.

Some implantable medical devices (IMDs) also sense and monitor cardiac EGMs. The electrodes used by IMDs to sense cardiac EGMs are typically integrated with a housing of the IMD and/or coupled to the IMD via one or more elongated leads. Example IMDs that monitor cardiac EGMs include pacemakers and implantable cardioverter-defibrillators, which may be coupled to intravascular or extravascular leads, as well as pacemakers with housings configured for implantation within the heart, which may be leadless. An example of pacemaker configured for intracardiac implantation is the Micra™ Transcatheter Pacing System, available from Medtronic plc. Some IMDs that do not provide therapy, e.g., implantable patient monitors, sense cardiac EGMs. One example of such an IMD is the Reveal LINQ™ Insertable Cardiac Monitor (ICM), available from Medtronic plc, which may be inserted subcutaneously. Such IMDs may facilitate relatively longer-term monitoring of patients during normal daily activities and may periodically transmit collected data to a network service, such as the Medtronic Carelink™ Network.

Some IMDs may include sensors and/or electrodes on one side of the device. Migration of the IMD, e.g., movement of the IMD after implantation such as translation and/or rotation of the IMD, may then reduce the amount/amplitude of cardiac EGMs sensed by the IMD. For example, a subcutaneous pocket may be formed during implantation of the IMD, and migration may occur post-implantation and before tissue is formed around the IMD in the pocket. In some cases, the IMD may be repositioned, e.g., via a subcutaneous procedure and/or by removing and replacing the IMD in the correct position and/or orientation. In some cases, the IMD may benefit from an absorbable antibacterial material and/or layer, e.g., to reduce infection of an IMD that has been repositioned. Further, the IMD may benefit from an absorbable antibacterial material and/or layer configured to reduce and/or eliminate migration of the IMD.

According to examples of this disclosure, an absorbable antibacterial material and/or layer is configured to be disposed on a housing of an IMD and configured to be compatible with an implantation tool of the IMD. In some examples, the absorbable antibacterial material may be disposed within a layer of material and configured to be absorbed by the patient when the IMD is implanted in the patient. In some examples, an absorbable antibacterial layer (e.g., including the absorbable antibacterial material) may be configured to be disposed on a housing of an IMD and configured to not interfere with a sensor of the IMD. For example, the absorbable antibacterial layer may be positioned, disposed, adhered, patterned, or the like, on at least a portion outer surface of the housing of the IMD not including a sensor. In some examples, the sensor may be an electrode connected to control circuitry that is configured to monitor a physiological parameter of a patient via the electrode, and the absorbable antibacterial layer is disposed on the housing so as to not interfere with a parameter sensed/detected by the electrode.

In some examples, the absorbable antibacterial material and/or layer is configured to be disposed on a housing of an external device and/or monitor. In some examples, the absorbable antibacterial layer may be configured to be disposed on a housing of an external device and configured to not interfere with a sensor of the external device. For example, the absorbable antibacterial layer may be positioned, disposed, adhered, patterned, or the like, on at least a portion outer surface of the housing of the external device not including a sensor, and that may also come into contact with the patient, allowing the absorbable antibacterial material to be absorbed by the patient. In some examples, the sensor may be an electrode of the external device that is connected to control circuitry that is configured to monitor a physiological parameter of a patient via the electrode, and the absorbable antibacterial layer is disposed on the housing so as to not interfere with a parameter sensed/detected by the electrode.

In some examples, the absorbable antibacterial layer may be configured to reduce migration of the IMD when the IMD is implanted within the patient. For example, the absorbable antibacterial layer may increase a friction between tissue of the patient and the IMD and reduce an amount of rotation and/or translation of the IMD, e.g., until tissue is formed around the IMD after implantation. In other examples, the absorbable antibacterial layer may be configured may reduce migration via providing a means of attaching the IMD to tissue of the patient. For example, the absorbable antibacterial layer may comprise a mesh layer configured to be adhered to the IMD housing and sutured to tissue of the patient.

According to the systems, articles, and techniques disclosed, the absorbable antibacterial layer is configured to be compatible with an implantation tool and/or device. The absorbable antibacterial layer is configured to be received within an implantation tool and delivered out of the implantation tool and into a patient, e.g., along with the IMD. For example, an implantation tool may include a channel configured to receive the IMD and a plunger slidably fitting within the channel and configured to push the IMD out of the channel to implant the IMD. The channel may include mechanical features, e.g., guides configured to hold and/or guide the IMD while it is pushed along the channel. The absorbable antibacterial layer may be configured to be disposed on the housing of the IMD and to not interfere with the mechanical features of the tool. For example, placing the IMD in an absorbable antibacterial bag, such as a Tyrx™ bag, may not allow the IMD to be implanted via the implantation tool because the bag would catch on the mechanical features of the tool, or would simply not fit within the channel of the tool, or the like. In contrast, and according to this disclosure, an absorbable antibacterial layer may be configured to be disposed on a portion of the IMD housing and be compatible with the implantation tool, e.g., to fit within the channel of the implantation tool while disposed on the IMD and to be implantable along with the IMD without interfering with mechanical features of the implantation tool. In some examples, the implantation tool may be a syringe.

FIG. 1 is a conceptual drawing illustrating an example medical system 10 in conjunction with a patient 12 according to various examples described in this disclosure. The systems, devices, and methods described in this disclosure may include examples configurations of an absorbable antibacterial layer 16 disposed on an IMD 14, as illustrated and described with respect to FIG. 1. For purposes of this description, knowledge of cardiovascular anatomy and functionality is presumed, and details are omitted except to the extent necessary or desirable to explain the context of the techniques of this disclosure. System 10 includes IMD 14 having absorbable antibacterial layer 16, implanted at or near the site of a heart 18 of a patient 12 and an external computing device 24. The systems, devices, and methods described herein may provide infection control and migration control of IMD 16. For example purposes, this disclosure may illustrate the IMD 14 having absorbable antibacterial layer 16 implanted at or near the site of a heart 18 of a patient 12; however, IMD 14 may also be inserted at any other suitable anatomical location including, but not limited to the head, neck, torso, upper extremities, and lower extremities.

The example techniques may be used with IMD 14, which may be in wireless communication with at least one of external device 24 and other devices not pictured in FIG. 1. In some examples, IMD 14 is implanted outside of a thoracic cavity of patient 12 (e.g., subcutaneously in the pectoral location illustrated in FIG. 1). IMD 14 may be positioned near the sternum near or just below the level of the heart of patient 12, e.g., at least partially within the cardiac silhouette. IMD 14 includes a plurality of electrodes 48 (FIG. 5) and is configured to sense a cardiac electrogram (EGM) via the plurality of electrodes. In some examples, IMD 14 takes the form of the LINQ™ ICM, or another ICM similar to, e.g., a version or modification of, the LINQ™ ICM. Although described primarily in the context of examples in which IMD 14 is an ICM, in various examples, IMD 14 may represent a cardiac monitor, a defibrillator, a cardiac resynchronization pacer/defibrillator, a pacemaker, an implantable pressure sensor, a neurostimulator, or any other implantable or external medical device.

In some examples, IMD 14 is defined by a length L, a width W and thickness or depth D and is in the form of an elongated rectangular prism wherein the length L is much larger than the width W, which in turn is larger than the depth D. In one example, the geometry of the IMD 14—in particular a width W greater than the depth D—is selected to allow IMD 14 to be inserted under the skin of the patient using a minimally invasive procedure and to remain in the desired orientation during insert. For example, IMD 14 may include a radial asymmetry (notably, a rectangular shape) along the longitudinal axis that maintains the device in the proper orientation following insertion. For example, in one example the spacing between electrode 48A and electrode 48B may range from 30 millimeters (mm) to 55 mm, 35 mm to 55 mm, and from 40 mm to 55 mm and may be any range or individual spacing from 25 mm to 60 mm. In another example the spacing between electrode 48A and electrode 48B may range from 15 mm to 30 mm, 17 mm to 28 mm, and from 20 mm to 28 mm and may be any range or individual spacing from 12 mm to 30 mm. In addition, IMD 14 may have a length L that ranges from 30 mm to about 70 mm. In other embodiments, the length L may range from 40 mm to 60 mm, 45 mm to 60 mm and may be any length or range of lengths between about 30 mm and about 70 mm. In some examples, IMD 14 may have a length L that ranges from 15 mm to about 35 mm, or from 20 mm to 30 mm, 22 mm to 30 mm and may be any length or range of lengths between about 15 mm and about 35 mm. In addition, the width W of a major surface of IMD 14, e.g., insulative cover 76 in the example shown, may range from 3 mm to 10 mm and may be any single or range of widths between 3 mm and 10 mm, or may range from 1.5 mm to 5 mm and may be any single or range of width between 1.5 mm and 5 mm. The thickness of depth D of IMD 14 may range from 2 mm to 9 mm, or from 1.5 mm to 4.5 mm. In other embodiments, the depth D of IMD 14 may range from 2 mm to 5 mm and may be any single or range of depths from 2 mm to 9 mm, or may range from 1 mm to 2.5 mm and may be any single or range of depts from 1 mm to 4.5 mm. In addition, IMD 14 according to an example of the present invention has a geometry and size designed for case of implant and patient comfort. Examples of IMD 14 described in this disclosure may have a volume of three cubic centimeters (cm) or less, 1.5 cubic cm or less or any volume between three and 1.5 cubic centimeters, or may have a volume of 1.5 cubic centimeters (cm) or less, 0.75 cubic cm or less or any volume between 1.5 and 0.75 cubic centimeters.

External device 24 may be a computing device with a display viewable by the user and an interface for providing input to external device 24 (i.e., a user input mechanism). In some examples, external device 24 may be a notebook computer, tablet computer, workstation, one or more servers, cellular phone, personal digital assistant, or another computing device that may run an application that enables the computing device to interact with IMD 14. External device 24 is configured to communicate with IMD 14 and, optionally, another computing device (not illustrated in FIG. 1), via wireless communication. External device 24, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies).

External device 24 may be used to configure operational parameters for IMD 14. External device 24 may be used to retrieve data from IMD 14. The retrieved data may include values of physiological parameters measured by IMD 14, indications of episodes of arrhythmia or other maladies detected by IMD 14, and physiological signals recorded by IMD 14. For example, external device 24 may retrieve cardiac EGM segments recorded by IMD 14, e.g., due to IMD 14 determining that an episode of arrhythmia or another malady occurred during the segment, or in response to a request to record the segment from patient 12 or another user. In some examples, one or more remote computing devices may interact with IMD 14 in a manner similar to external device 24, e.g., to program IMD 14 and/or retrieve data from IMD 14, via a network.

In various examples, IMD 14 may include one or more additional sensor circuits configured to sense a particular physiological or neurological parameter associated with patient 12, or may comprise a plurality of sensor circuits, which may be located at various and/or different positions relative to patient 12 and/or relative to each other and may be configured to sense one or more physiological parameters associated with patient 12.

For example, IMD 14 may include a sensor operable to sense a body temperature of patient 12 in a location of the IMD 14, or at the location of the patient where a temperature sensor coupled by a lead to IMD 14 is located. In another example, IMD 14 may include a sensor configured to sense motion, such as steps taken by patient 12 and/or a position or a change of posture of patient 12. In various examples, IMD 14 may include a sensor that is configured to detect breaths taken by patient 12. In various examples, IMD 14 may include a sensor configured to detect heartbeats of patient 12. In various examples, IMD 14 may include a sensor that is configured to measure systemic blood pressure of patient 12.

In some examples, one or more of the sensors comprising IMD 14 may be implanted within patient 12, that is, implanted below at least the skin level of the patient. In some examples, one or more of the sensors of IMD 14 may be located externally to patient 12, for example as part of a cuff or as a wearable device, such as a device imbedded in clothing that is worn by patient 12. In various examples, IMD 14 may be configured to sense one or more physiological parameters associated with patient 12, and to transmit data corresponding to the sensed physiological parameter or parameters to external device 24, as represented by the lightning bolt coupling IMD 14 to external device 24.

Transmission of data from IMD 14 to external device 24 in various examples may be performed via wireless transmission, using for example any of the formats for wireless communication described above. In various examples, IMD 14 may communicate wirelessly to an external device (e.g., an instrument or instruments) other than or in addition to external device 24, such as a transceiver or an access point that provides a wireless communication link between IMD 14 and a network. Examples of communication techniques used by any of the devices described above with respect to FIG. 1 may include radiofrequency (RF) telemetry, which may be an RF link established via Bluetooth®, Wi-Fi, or medical implant communication service (MICS).

In some examples, system 10 may include more or fewer components than depicted in FIG. 1. For example, in some examples, system 10 may include multiple additional IMDs, such as implantable pacemaker devices or other IMDs, implanted within patient 12. In these examples, IMD 14 may function as a hub device for the other IMDs. For example, the additional IMDs may be configured to communicate with the IMD 14, which would then communicate to the external device 24, such as a user's smartphone, via a low-energy telemetry protocol. IMD 14 may provide a theoretically infinite energy capacity, in that IMD 14 may not need to be replaced or otherwise removed. Accordingly, IMD 14 may provide the ability to more-frequently telemeter information, as well as more-active titration of therapies.

For the remainder of the disclosure, a general reference to a medical device system may refer collectively to include any examples of medical device system 10, a general reference to IMD 14 may refer collectively to include any examples of IMD 14, a general reference to sensor circuits may refer collectively to include any examples of sensor circuits of IMD 14, and a general reference to an external device may refer collectively to any examples of external device 24.

Figure 2:
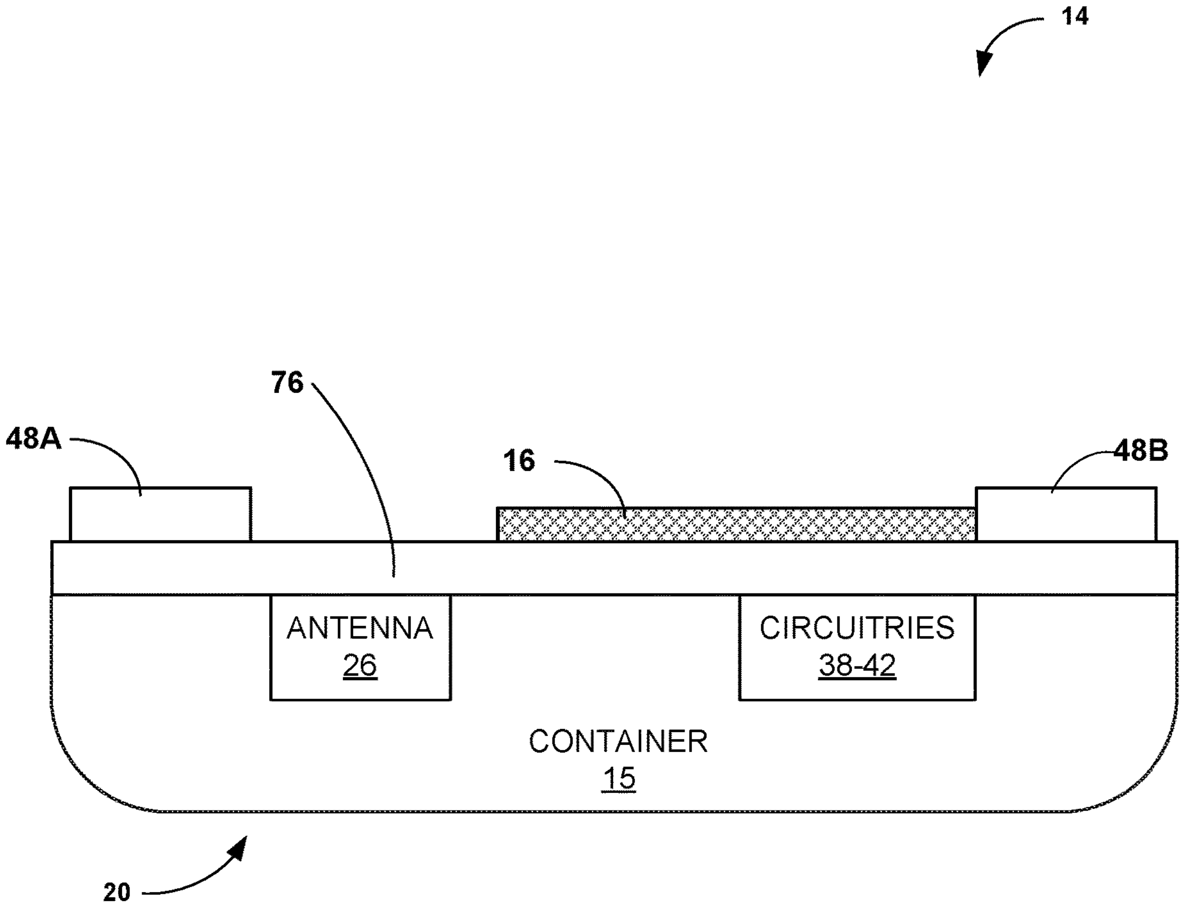
FIG. 2 is a conceptual side-view diagram illustrating an example configuration of the implantable medical device (IMD) and absorbable antibacterial layer of the medical system of FIG. 1, according to various examples described in this disclosure.

FIG. 2 is a conceptual side-view diagram illustrating an example configuration of the implantable medical device (IMD) 14 and absorbable antibacterial layer 16 of medical system 10 of FIG. 1. In the example shown in FIG. 2, IMD 10 may include a leadless, subcutaneously implantable monitoring device having a container 15 and an insulative cover 76. Electrode 48A and electrode 48B (collectively "electrodes 48") may be formed or placed on an outer surface of cover 76. Circuitries 36-42, described below with respect to FIG. 3, may be formed or placed on an inner surface of cover 76, or within container 15. In the illustrated example, antenna 26 is formed or placed on the inner surface of cover 76 but may be formed or placed on the outer surface in some examples. In some examples, insulative cover 76 may be positioned over an open container 15 such that container 15 and cover 76 form housing 20 and enclose antenna 26 and circuitries 36-42 and protect the antenna and circuitries from fluids such as body fluids.

One or more of antenna 26 or circuitries 36-42 may be formed on the inner side of insulative cover 76, such as by using flip-chip technology. Insulative cover 76 may be flipped onto a container 15. When flipped and placed onto container 15, the components of IMD 10 formed on the inner side of insulative cover 76 may be positioned in a gap 78 defined by container 15. Electrodes 48 may be electrically connected to sensing circuitry 42 (illustrated in FIG. 3) through one or more vias (not shown) formed through insulative cover 76. Insulative cover 76 may be formed of sapphire (i.e., corundum), glass, parylene, and/or any other suitable insulating material. Container 15 may be formed from titanium or any other suitable material (e.g., a biocompatible material). Electrodes 48 may be formed from any of stainless steel, titanium, platinum, iridium, or alloys thereof. In addition, electrodes 48 may be coated with a material such as titanium nitride or fractal titanium nitride, although other suitable materials and coatings for such electrodes may be used.

Absorbable antibacterial layer 16 is disposed on housing 20. In the example shown, absorbable antibacterial layer 16 is disposed on insulative cover 76. In some examples, absorbable antibacterial layer 16 may be disposed on all or a portion of any outer surface of IMD 14 and/or housing 20. For example, absorbable antibacterial layer 16 may be disposed on all or a portion of container 15, insulative cover 76, or at least a portion of both container 15 and insulative cover 76. In some examples, absorbable antibacterial layer 16 may be disposed on greater than or equal to 20% of the surface area of housing 20, on greater than or equal to 50% of the surface area of housing 20, on greater than or equal to 75% of the surface area of housing 20, on greater than or equal to 90% of the surface area of housing 20, or any suitable surface area of housing 20. In some examples, absorbable antibacterial layer 16 may be disposed on substantially all of housing 20 surface area that is not a sensor electrode, e.g., electrode 48A or 48B. In some examples, absorbable antibacterial layer 16 may be disposed on greater than 55% of housing 20 surface area that is not electrode 48A or 48B and in some other examples, absorbable antibacterial layer 16 may be disposed on greater than 90% of housing 20 surface area that is not electrode 48A or 48B.

In some examples, absorbable antibacterial layer 16 may be disposed of an amount of surface area of housing 20 that corresponds to a period of time over which the antibacterial material is absorbed by the patient. For example, IMD 14 including absorbable antibacterial layer 16 disposed on 20% of the surface area of housing 20 may be configured to deliver (via absorption) the antibacterial material to the patient, when IMD 14 is implanted, over a first time period, and MD 14 including absorbable antibacterial layer 16 disposed on 80% of the surface area of housing 20 may be configured to deliver the antibacterial material to the patient, when IMD 14 is implanted, over a second time period that is greater than the first time period. In some examples, IMD 14 including absorbable antibacterial layer 16 is be configured to be received within an implantation tool and delivered out of the implantation tool and into a patient, e.g., as further illustrated and described below at FIGS. 4-8.

In some examples, the absorbable antibacterial layer 16 is configured to provide absorbable antibacterial material over a period of time. For example, absorbable antibacterial layer 16 may be configured such that between 45% to 55% of the absorbable antibacterial material comprising absorbable antibacterial layer 16 is absorbed by the patient within 30 to 60 days. In some examples, absorbable antibacterial layer 16 may be configured such that between 65% to 85% of the absorbable antibacterial material comprising absorbable antibacterial layer 16 is absorbed by the patient after 90 days Absorbable antibacterial layer 16 may be configured to not interfere with the efficacy of IMD 14, e.g., electrodes 48, receiving a physiological signal. In some examples, absorbable antibacterial layer 16 may be configured to be substantially transparent to the physiological signal, e.g., such that electrodes 48 may receive the physiological signal though absorbable antibacterial layer 16. In other examples, absorbable antibacterial layer 16 may be disposed on housing 20 so as to not interfere with electrodes 48 receiving the physiological signal. In the example shown, absorbable antibacterial layer 16 is disposed on an area of insulative cover 76 not including electrodes 48. In some examples, absorbable antibacterial layer 16 is configured to not interfere with IMD 14, e.g., antenna 26 receiving and/or sending communication signals. For example, absorbable antibacterial layer 16 may be disposed on an area of insulative cover 76 that is not opposite antenna 26, e.g., absorbable antibacterial layer 16 is not disposed over antenna 26 as illustrated in FIG. 2. In some examples, absorbable antibacterial layer 16 may be disposed on housing 20 in a pattern. For example, antibacterial layer 16 may be disposed on a first area of housing 20 and not disposed on a second area of housing 20. In some examples, absorbable antibacterial layer 16 may be etched to form the pattern. For example, absorbable antibacterial layer 16 may be disposed on housing 20 and may be removed and/or etched away at one or more areas of housing 20, e.g., electrode 48 areas and/or areas opposite and/or including antenna 26. In other examples, absorbable antibacterial layer 16 may be patterned via etching or any suitable method, and then disposed on housing 20. For example, the pattern of patterned absorbable antibacterial layer 16 may align with features of IMD 14, e.g., etched away and/or removed portions of absorbable antibacterial layer 16 may align with one or more of electrodes 48, antenna 26, or any other suitable feature.

Absorbable antibacterial layer 16 may be configured to prevent and/or reduce growth of bacteria in patient 12. In some examples, absorbable antibacterial layer 16 may comprise an antibiotic, such as rifampin, minocycline, or any suitable antibiotic.

Absorbable antibacterial layer 16 may be configured to prevent and/or reduce migration of IMD 14 implanted in patient 12. For example, absorbable antibacterial layer 16 may comprise surface configured to increase friction and/or a force required to move IMD 14 within patient 14. In some examples, absorbable antibacterial layer 16 may comprise a pattern or surface relief structure, a mesh, a mesh including a plurality of filaments, a woven material, a nonwoven material, or any suitable material and/or surface configured to prevent and/or reduce migration of IMD 14 within patient 12. In some examples, absorbable antibacterial layer 16 is configured to receive a suture, e.g., absorbable antibacterial layer 16 may be attached to IMD 14 (such as by an adhesive) and absorbable antibacterial layer 16 may also be attached to tissue of patient 12, such as by a suture. In some examples, absorbable antibacterial layer 16 is configured to promote and/or receive ingrowth of tissue within absorbable antibacterial layer 16, e.g., so as to reduce and/or prevent migration of IMD 14 within patient 12.

In some examples, absorbable antibacterial layer 16 is configured to release from tissue of patient 14, e.g., upon removal of IMD 14 from patient 12. For example, absorbable antibacterial layer 16 may be configured to be sutured to tissue of patient 12, and after a period of time, e.g., after tissue is formed in a pocket that IMD 14 and absorbable antibacterial layer 16 is implanted into within patient 14, absorbable antibacterial layer 16 may then weaken and/or at least partially dissolve such that absorbable antibacterial layer 16 may easily pull away from tissue and/or sutures when it comes time to remove IMD 14 from patient 14. In some examples, absorbable antibacterial layer 16 may be configured to prevent and/or reduce ingrowth of tissue within absorbable antibacterial layer 16.

In some examples, absorbable antibacterial layer 16 is configured to attach to housing 20. For example, absorbable antibacterial layer 16 may be adhered to housing 20 via an adhesive. In other examples, absorbable antibacterial layer 16 may be configured to be disposed on housing 20 via a compression fit. For example, absorbable antibacterial layer 16 may form a container or "sock" configured to receive IMD 14. Absorbable antibacterial layer 16 may be configured to stretch upon receiving IMD 14, and to apply a compressive force on IMD 14 and thereby remain attached to IMD 14 via a compression fit and/or friction fit. In such examples, absorbable antibacterial layer 16 may be patterned and/or include open areas corresponding to features such as electrodes 48 and/or antenna 26, e.g., to leave areas of housing 20 corresponding to electrodes 48 and/or antenna 26 open or uncovered by absorbable antibacterial layer 16.

In some examples, absorbable antibacterial layer 16 may comprise a material layer having a thickness, e.g., at least 25 micrometers thick, at least 100 micrometers thick, at least 1 millimeter thick, at least 5 millimeters thick, at least 10 millimeters thick, or any suitable thickness. The material layer may include an absorbable antibacterial material (such as rifampin, minocycline, or any suitable antibiotic) disposed on an outer surface of the material layer and/or disposed within the material layer. In some examples, the material layer may comprise a woven or nonwoven material, and the absorbable antibacterial material may be on a surface of one or more fibers or within one or more fibers of the material. In some examples, the material layer may comprise a mesh. In some examples, the absorbable antibacterial layer 16 is configured to be cut, folded, and/or resized, e.g., by a clinician and/or user using a scissors or blade. In some examples, absorbable antibacterial layer 16 may comprise Tyrx.™ The absorbable antibacterial material is configured to be absorbed by the patient from the material layer when absorbable antibacterial layer 16 is implanted within the patient.

In some examples, absorbable antibacterial layer 16 may be provided to a clinician and/or user as part of a kit. For example, a kit may include a sterile container configured to receiver any or all of IMD 14, an implantation tool (such as described below at FIGS. 4-8), absorbable antibacterial layer 16, and optionally and adhesive configured to attached absorbable antibacterial layer 16 to a surface of IMD 14. In some examples, the sterile container may comprise a sterile bag. In some examples, absorbable antibacterial layer 16 may come as a kit pre-attached to IMD 14. For example, absorbable antibacterial layer 16 may be a "sock" and friction fit with IMD 14, as described above. In other examples, absorbable antibacterial layer 16 may be attached and/or laminated via an adhesive to one or more sides or surfaces of IMD 14. In still other examples, absorbable antibacterial layer 16 may be provided as one or more sheets, which may optionally be cuttable, along with a separate adhesive layer configured to be attached to absorbable antibacterial layer 16, and then to IMD 14, or vice versa.

Figure 3:
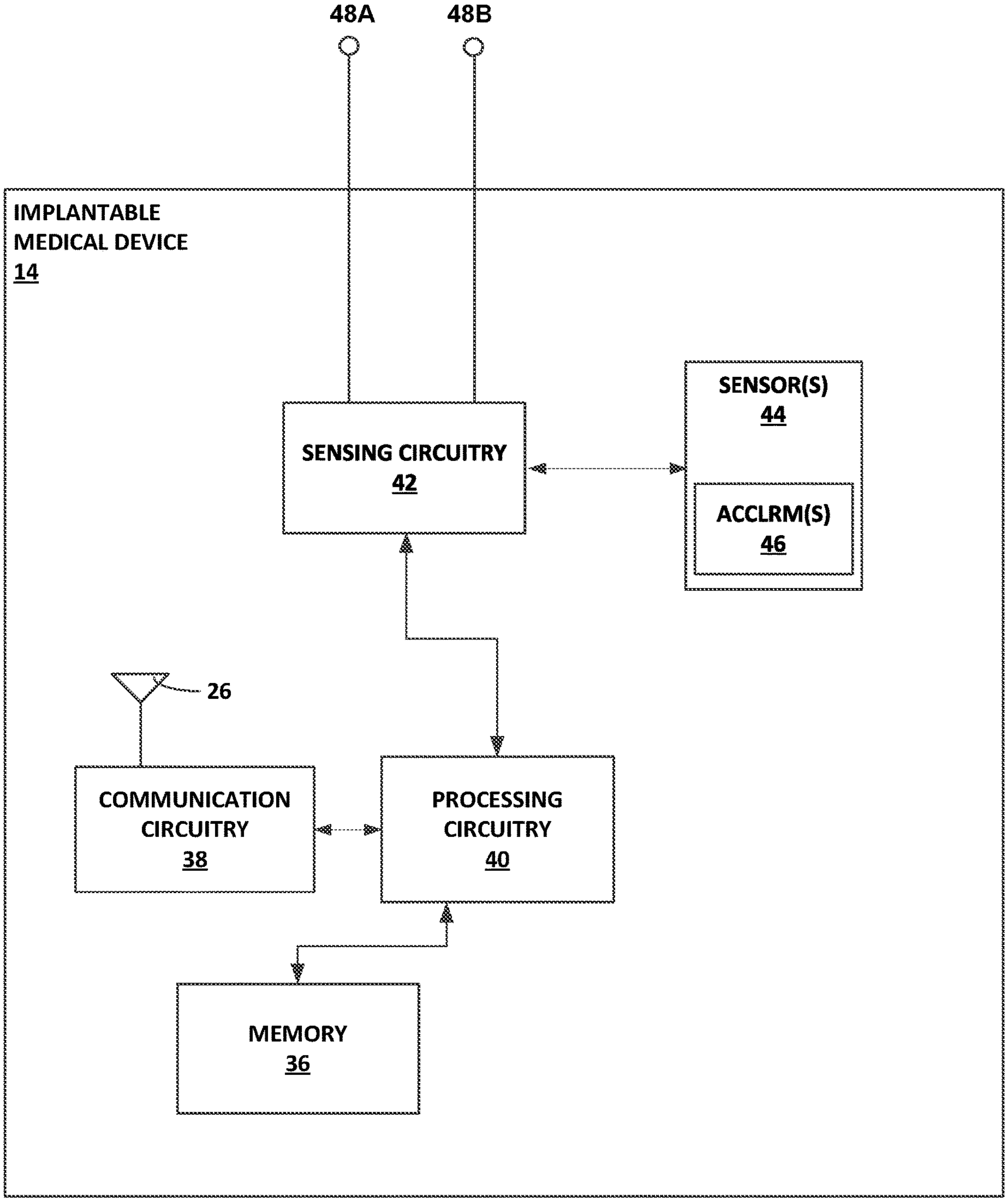
FIG. 3 is a functional block diagram illustrating an example configuration of the implantable medical device (IMD) of the medical system of FIG. 1, according to various examples described in this disclosure.

FIG. 3 is a functional block diagram illustrating an example configuration of the implantable medical device (IMD) and of the medical system of FIG. 1. In the illustrated example, IMD 14 includes processing circuitry 40, memory 36, communication circuitry 38, communication antenna 26, sensing circuitry 42, sensor(s) 44, accelerometer(s) 46, and electrodes 48A and 48B (collectively, "electrodes 48"). Although the illustrated example includes two electrodes 48, IMDs including or coupled to one electrode 48, or more than two electrodes 48, may implement the techniques of this disclosure in some examples.

Processing circuitry 40 may include fixed function circuitry and/or programmable processing circuitry. Processing circuitry 40 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 40 may include multiple components, such as any combination of one or more microprocessors, one or more controllers, one or more DSPs, one or more ASICs, or one or more FPGAs, as well as other discrete or integrated logic circuitry. The functions attributed to processing circuitry 40 herein may be embodied as software, firmware, hardware or any combination thereof.

Sensing circuitry 42 is coupled to electrodes 48 and is configured to monitor one or more physiological parameters of a patient. Sensing circuitry 42 may sense signals from electrodes 48, e.g., to produce a cardiac EGM, in order to facilitate monitoring the electrical activity of the heart. Sensing of a cardiac EGM may be done to determine heart rates or heart rate variability, or to detect arrhythmias (e.g., tachyarrhythmias or bradycardia). Sensing circuitry 42 may additionally monitor impedance or other electrical phenomena via electrodes 48. Sensing circuitry 42 also may monitor signals from sensors 44, which may include one or more accelerometers 46, pressure sensors, and/or optical sensors, as examples. In some examples, sensing circuitry 42 may include one or more filters and amplifiers for filtering and amplifying signals received from electrodes 48 and/or sensors 44. In some examples, sensing circuitry 42 may sense or detect physiological parameters, such as heart rate, blood pressure, respiration, and other physiological parameters associated with a patient.

Sensing circuitry 42 and/or processing circuitry 40 may be configured to detect cardiac depolarizations (e.g., P-waves of atrial depolarizations or R-waves of ventricular depolarizations) when the cardiac EGM amplitude crosses a sensing threshold. For cardiac depolarization detection, sensing circuitry 42 may include a rectifier, filter, amplifier, comparator, and/or analog-to-digital converter, in some examples. In some examples, sensing circuitry 42 may output an indication to processing circuitry 40 in response to sensing of a cardiac depolarization. In this manner, processing circuitry 40 may receive detected cardiac depolarization indicators corresponding to the occurrence of detected R-waves and P-waves in the respective chambers of heart. Processing circuitry 40 may use the indications of detected R-waves and P-waves for determining inter-depolarization intervals, heart rate, and detecting arrhythmias, such as tachyarrhythmias and asystole.

Sensing circuitry 42 may also provide one or more digitized cardiac EGM signals to processing circuitry 40 for analysis, e.g., for use in cardiac rhythm discrimination. In some examples, processing circuitry 40 may store the digitized cardiac EGM in memory 36. Processing circuitry 40 of IMD 14, and/or processing circuitry of another device that retrieves data from IMD 14, may analyze the cardiac EGM.

Communication circuitry 38 may include any suitable hardware, firmware, software or any combination thereof for communicating with another device, such as external device 24, another networked computing device, or another IMD or sensor. Under the control of processing circuitry 40, communication circuitry 38 may receive downlink telemetry from, as well as send uplink telemetry to external device 24 or another device with the aid of an internal or external antenna, e.g., antenna 26. In addition, processing circuitry 40 may communicate with a networked computing device via an external device (e.g., external device 24 of FIG. 1) and a computer network, such as the Medtronic CareLink® Network. Antenna 26 and communication circuitry 38 may be configured to transmit and/or receive signals via inductive coupling, electromagnetic coupling, Near Field Communication (NFC), Radio Frequency (RF) communication, Bluetooth, Wi-Fi, or other proprietary or non-proprietary wireless communication schemes. Communication antenna 26 may telemeter data at a high frequency, such as around 2.4 gigahertz (GHz).

In some examples, memory 36 includes computer-readable instructions that, when executed by processing circuitry 40, cause IMD 14 and processing circuitry 40 to perform various functions attributed to IMD 14 and processing circuitry 40 herein. Memory 36 may include any volatile, non-volatile, magnetic, optical, or electrical media, such as a random-access memory (RAM), read-only memory (ROM), non-volatile RAM (NVRAM), electrically crasable programmable ROM (EEPROM), flash memory, or any other digital media. Memory 36 may store, as examples, programmed values for one or more operational parameters of IMD 14 and/or data collected by IMD 14, e.g., posture, heart rate, activity level, respiration rate, and other parameters, as well as digitized versions of physiological signals sensed by IMD 14, for transmission to another device using communication circuitry 38.

In the illustrated example, IMD 14 includes processing circuitry 40 and an associated memory 36, sensing circuitry 42, one or more sensors 44, and the communication circuitry 38 coupled to antenna 26 as described above. However, IMD 14 need not include all of these components, or may include additional components.

Figure 4:
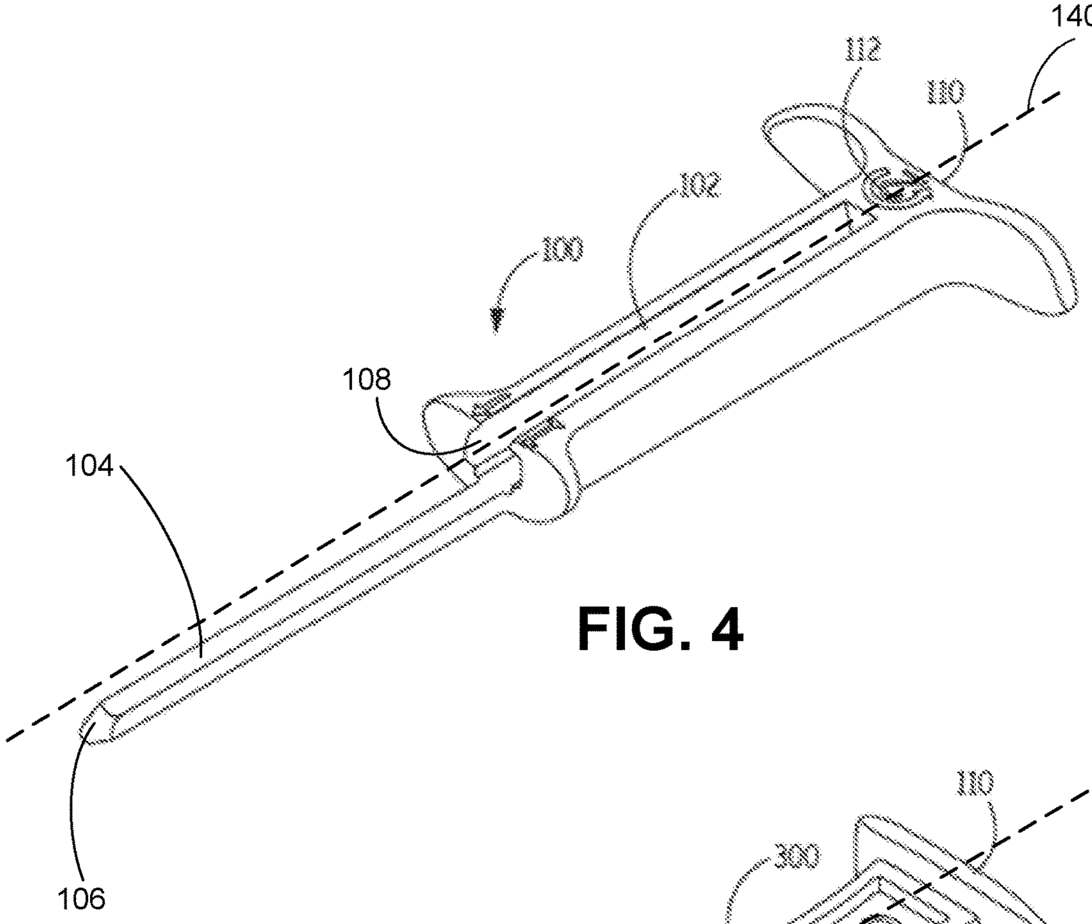
FIG. 4 is a perspective view of an example implantation tool handle, according to various examples described in this disclosure.
Figure 5:
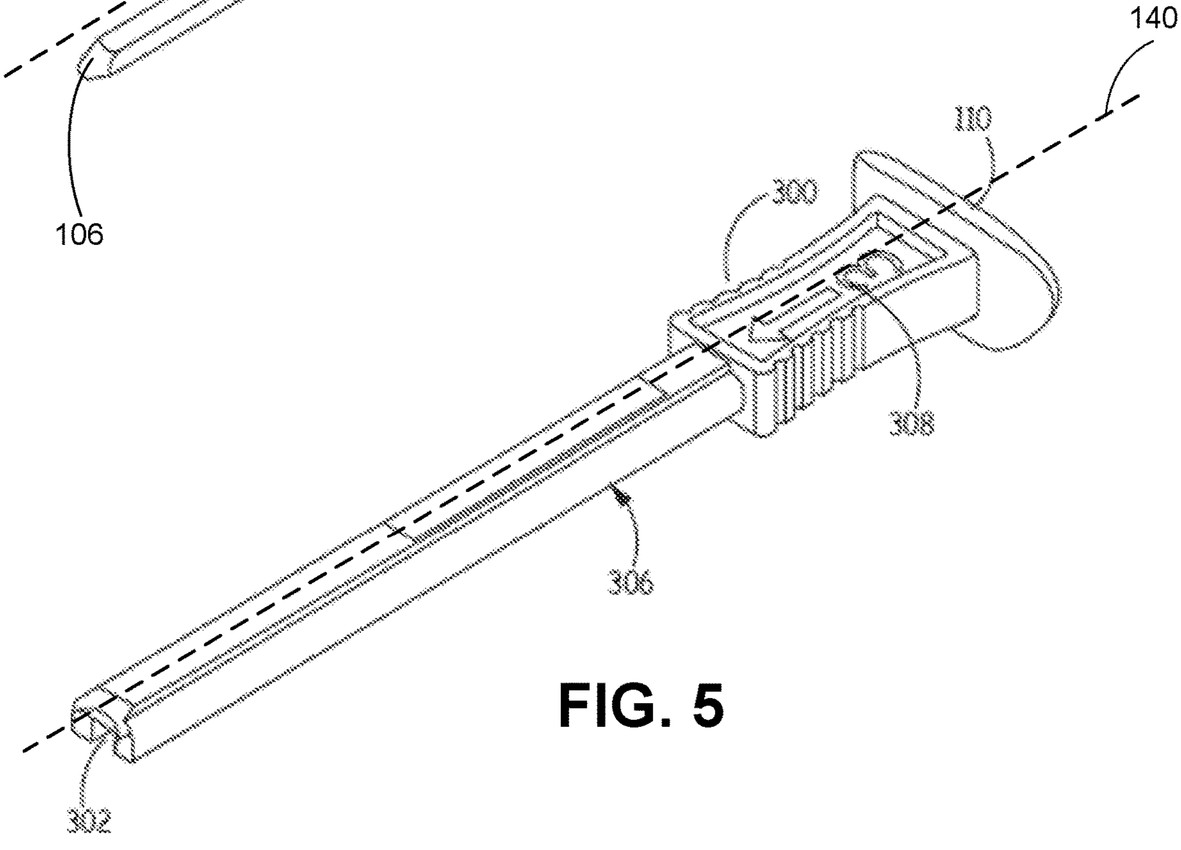
FIG. 5 is a perspective view of an example implantation tool plunger, according to various examples described in this disclosure.

FIGS. 4-5 are perspective views of an example implantation tool handle 100 and plunger 300, respectively, according to exemplary embodiments of the invention. Together, handle 100 and plunger 300 may comprise an implantation tool configured to receive a medical device (e.g., IMD 14) within a channel of the implantation tool. FIGS. 4-5 illustrate the handle 100 and the plunger 300 prior to insertion of plunger 300 into handle 100. To insert plunger 300 into handle 100, the distal end 302 of plunger 300 may be inserted into an opening in the proximal end 110 of handle 100 and into the channel 102 of the handle.

Handle 100 (also referred to as tool body 100 herein) may define a longitudinal axis 140 and channel 102 extending along longitudinal axis 140. Channel 102 may include a distal opening 108, and may be configured to receive a medical device, e.g., IMD 14 including absorbable antibacterial layer 16. For example, IMD 14 including absorbable antibacterial layer 16 may be inserted into the distal opening 108 of channel 102 and advanced proximally until IMD 14 including absorbable antibacterial layer 16 is located adjacent an internal stop surface (not illustrated) within handle 100. An open, upper portion of channel 102 may allow visual verification that IMD 14 including absorbable antibacterial layer 16 is properly inserted into channel 102. A tunneler 104 may extend distally along longitudinal axis 140 and adjacent distal opening 108 of channel 102. A distal end 106 of tunneler 104 may be configured to be placed into an incision within a patient, e.g., with an upper surface of tunneler 104 facing outward of the patient's body. Tunneler 104 may be configured to be advanced within the patient to provide blunt dissection of the subcutaneous tissue of the patient, e.g., advanced distally until distal opening 108 is substantially near the incision. Handle 100 may then be rotated 180 degrees about axis 140 such that tunneler 104 may assist in temporarily enlarging the incision (e.g., via pressure applied to handle 100). IMD 14 including absorbable antibacterial layer 16 may then be advanced distally within channel 102, and out of distal opening 108 and into the incision and dissected tissue of the patient along tunneler 104, by distal movement of plunger 300, e.g., until IMD 14 including absorbable antibacterial layer 16 is properly located within the tissue and displaced distally a short distance from the opening of the incision. A logo 112 assists in reminding the physician to rotate handle 100 prior to insertion of plunger 300 and advancement of the device.

Plunger 300 may be provided with a groove 306 running the length of the lower surface of plunger 300 up to a distal stop surface of projection 114 (FIG. 6E), and plunger 300 may be configured to slidably fit within channel 102 and to be movable within channel 102. The opening in proximal end 110 of the handle includes a protrusion corresponding to the groove in the lower surface of plunger 300, assuring its proper orientation within handle 100. A marking 308 adjacent proximal end 310 of plunger 300 assists a physician in determining that plunger 300 is in the proper orientation for insertion into handle 100.

Plunger 300 may be advanced distally, pushing a proximal end of IMD 14 including absorbable antibacterial layer 16 within channel 102 into an incision within the patient and along the then inward facing surface of tunneler 104. The IMD 14 including absorbable antibacterial layer 16 follows the path defined by tunneler 104 to assure proper placement within the tissue of the patient. After insertion of IMD 14 including absorbable antibacterial layer 16, handle 100 and plunger 300 are removed, e.g., tunneler 104 is removed from within the patient.

Various medical grade materials may be used to form the various parts of the implantation tool, for example, plastics, metals, rubber, sanitizable materials, etc. Exemplary embodiments of the implantation tool may be inexpensive, disposable. The implantation tool may also be configured to be used with known automated injection systems, which use, e.g., compressed air or other inert gases to operate plunger 300 or in place of plunger 300.

FIGS. 6A-6E are distal end, cut-away, top, bottom and proximal end views, respectively, of tool handle 100. In the examples shown, tool handle 100 includes projection 114. Projection 114 provides a distal facing stop surface limiting the insertion of IMD 14 including absorbable antibacterial layer 16 into channel 102. Projection 114 is further configured to engage groove 306 in a lower surface of plunger 300, e.g., for proper orientation of plunger 300 within handle 100. Projection 114 also provides a proximal facing stop surface limiting distal movement of plunger 300. Handle 100 may also optionally include a slot 116 in its lower surface (e.g., a lower surface at least partially defining channel 102), through which advancement of plunger 300 and IMD 14 including absorbable antibacterial layer 16 may be observed.

Figure 6A:
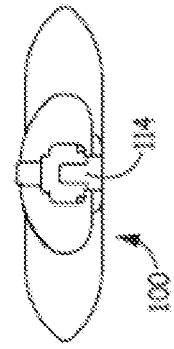
FIG. 6A is a distal end view of the example tool handle of FIG. 4, according to various examples described in this disclosure.
Figure 6E:
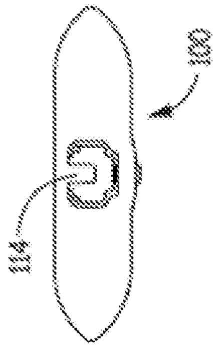
FIG. 6E is a proximal end view of the example tool handle of FIG. 4, according to various examples described in this disclosure.
Figure 6D:
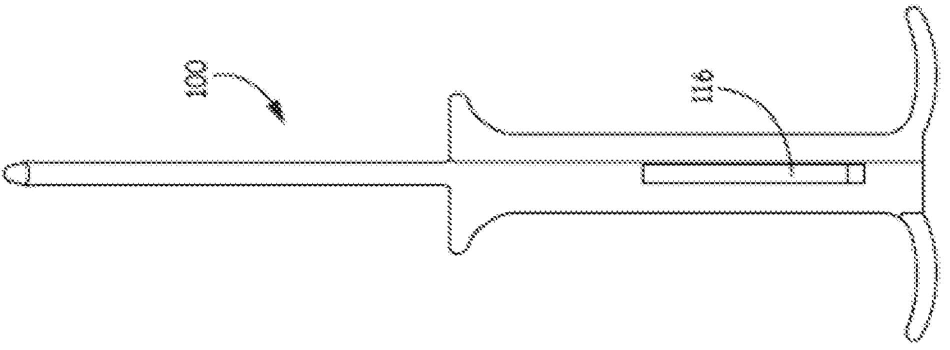
FIG. 6D is a bottom view of the example tool handle of FIG. 4, according to various examples described in this disclosure.
Figure 6C:
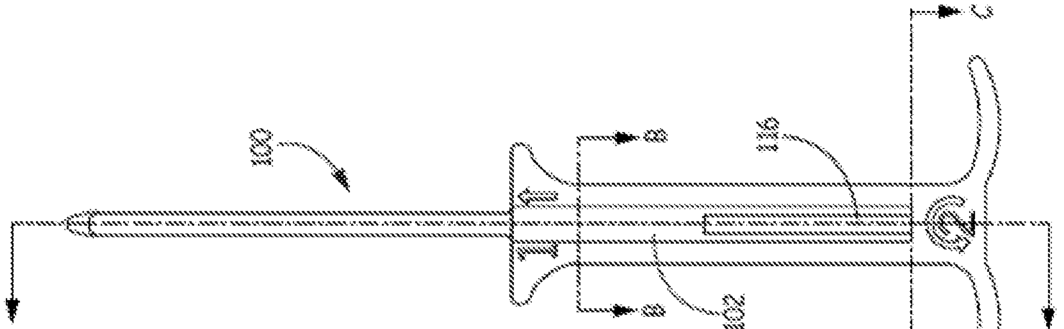
FIG. 6C is a top view of the example tool handle of FIG. 4, according to various examples described in this disclosure.
Figure 6B:
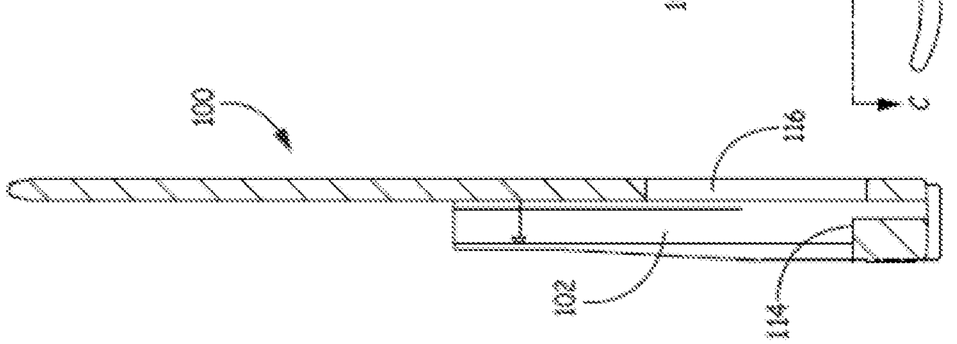
FIG. 6B is a cut-away view of the example tool handle of FIG. 4, according to various examples described in this disclosure.
Figure 7A:
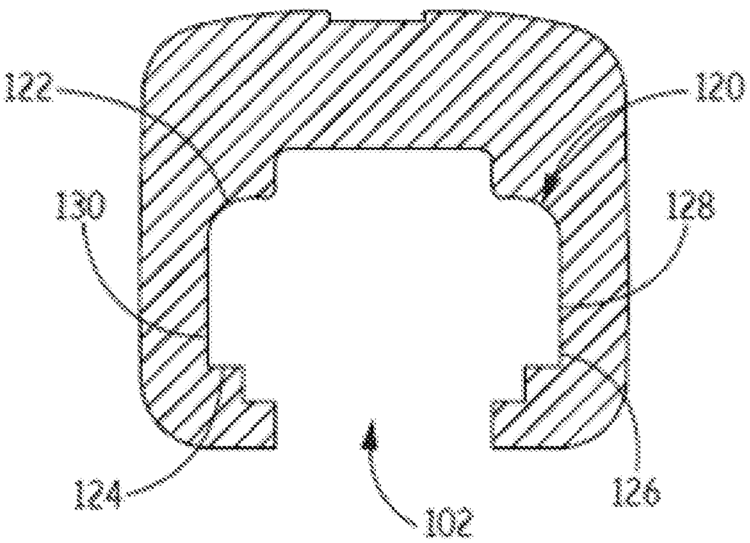
FIG. 7A is a cross-sectional view of the example tool handle of FIG. 4 along line B-B as illustrated in FIG. 6C, according to various examples described in this disclosure.
Figure 7B:
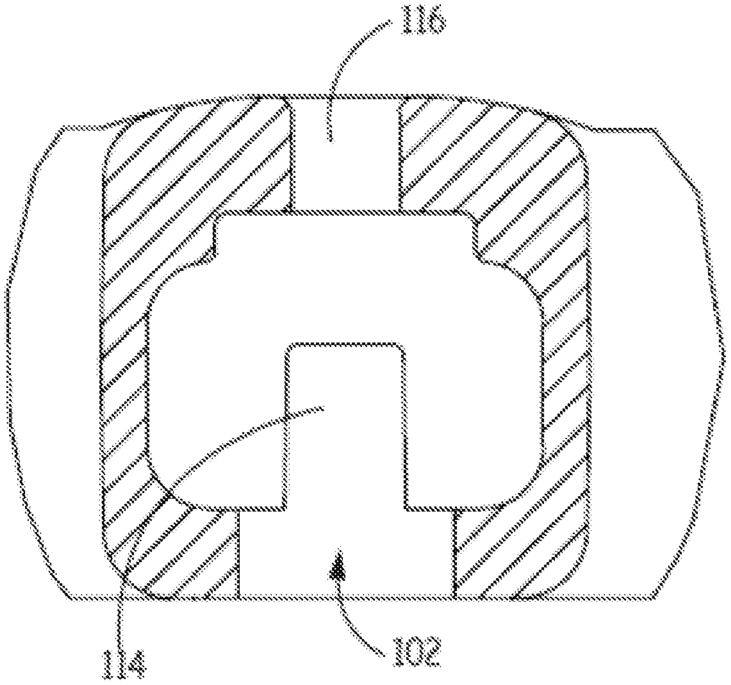
FIG. 7B is a cross-sectional view of the example tool handle of FIG. 4 along line C-C as illustrated in FIG. 6C, according to various examples described in this disclosure.

FIG. 7A is a cross-sectional view of tool handle 100 along line B-B as illustrated in FIG. 6C, and FIG. 7B is a cross-sectional view of tool handle 100 along line C-C as illustrated in FIG. 6C. FIG. 7A illustrates the arrangement of the inner corner surfaces 120, 122, 124 and 126. These surfaces, along with side surfaces 128 and 130, are arranged to generally correspond to the corners and the side surfaces of IMD 14 including absorbable antibacterial layer 16, preventing rotation of IMD 14 including absorbable antibacterial layer 16 within handle 100. FIG. 7B illustrates the distal facing surface of projection 114.

Figure 8:
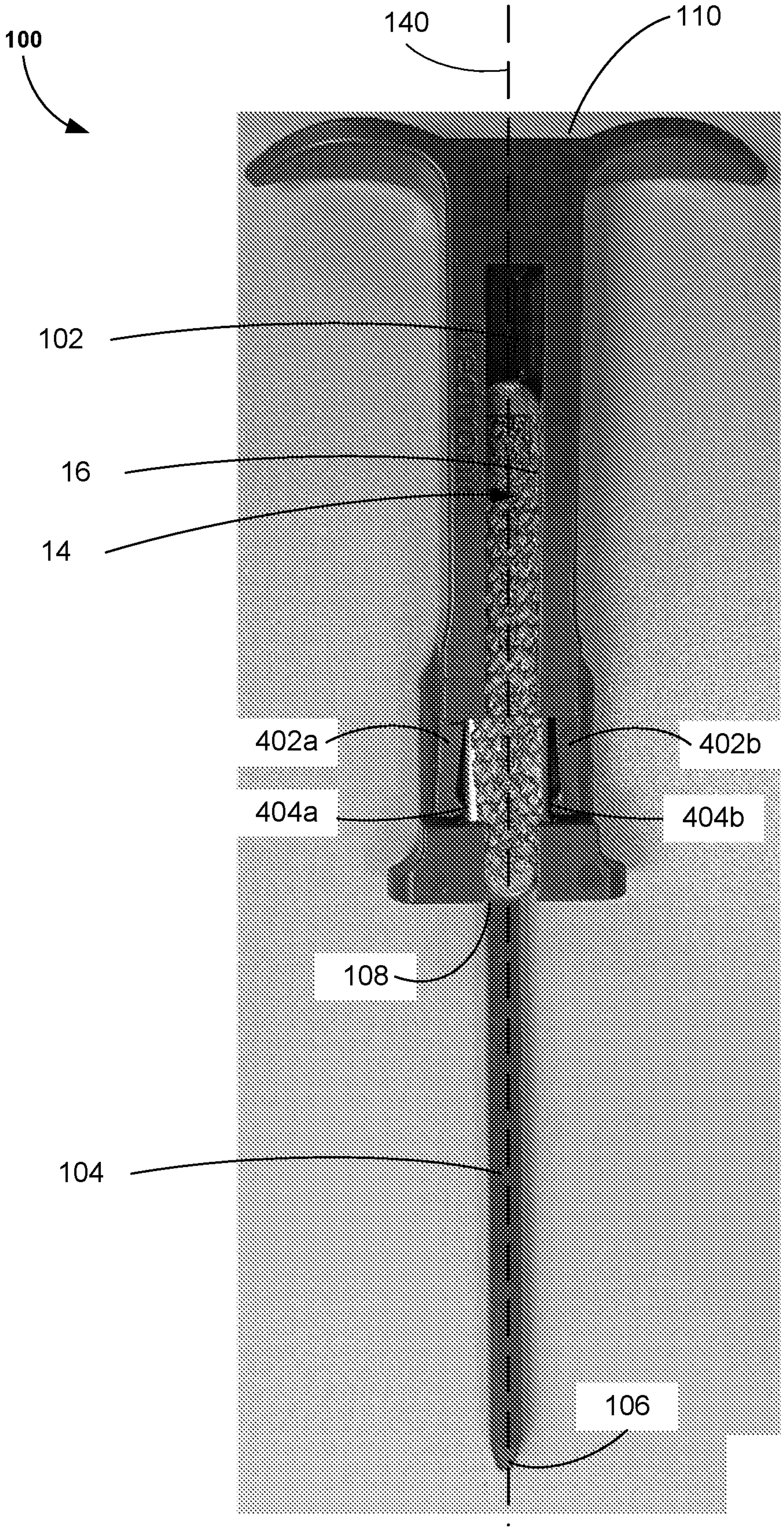
FIG. 8 is a perspective view of another example implantation tool handle with an example IMD including an example absorbable antibacterial layer received within a channel of the implantation tool handle, according to various examples described in this disclosure.

FIG. 8 is a perspective view of another example implantation tool handle 400 with IMD 14 including absorbable antibacterial layer 16 received within channel 102, according to various examples described in this disclosure. of another example implantation tool handle 400 with IMD 14 including absorbable antibacterial layer 16 received within channel 102, according to various examples described in this disclosure. Handle 400 may be substantially similar to handle 100 described above, with the exception that handle 400 includes guides 402*a* and 402*b* (collectively, "guides 402).

Guides 402 are configured to releasably hold IMD 14 within the implantation tool, e.g., channel 102, via a friction fit. Guides 402 may be configured to apply a force and/or pressure to IMD 14 via a spring force, e.g., guides 402 may be, or include, spring-loaded lever arms with contact points 404*a* and 404*b* (collectively, "contact points 404"). Guides 402 may cause contacts points 404 to apply a force to opposing sides of IMD 14. For example, as IMD 14 is pushed out of distal opening 108 and into the incision into the patient, the force applied to the opposing sides of IMD 14 by guides 402 may provide support to a proximal portion if IMD 14 as a distal portion of IMD 14 exits channel 102 and enters the patient (e.g., a "tissue pocket" created at least partially by tunneler 104 as described above). In some examples, guides 402 may be configured to retain IMD 14 within channel 14. For example, IMD 14 may be loaded within channel 102, e.g., by a user and/or clinician introducing IMD 14 into channel 102 via distal opening 108 and pushing IMD 14 in the proximal direction until the distal end of IMD 14 is proximal to contact points 404. Guides 402 may be configured to position contact points 404 within channel 402 so as to retain IMD 14 within channel 102, e.g., contact points 402 may block IMD 14 from sliding out of distal opening 108. Guides 402 may be configured open when a threshold amount of force is applied to contact points 404, e.g., via plunger 300 pushing IMD 14 in the distal direction. Contact points 404 may then separate laterally allowing IMD 14 to move distally within channel 102 while guides 402 cause contact points 404 to apply a force to each opposing side of IMD 14 as it moves through the channel. The lateral force applied by contact points 404 to the opposing sides of IMD 14 cause a friction force opposing the motion of IMD 14 within channel 102, with the amount of friction proportional to the amount of force applied by guides 402 as dependent on the shape and amount of surface area of contact points 404 contacting the opposing side of IMD 14. In additional to providing lateral stability during insertion, the friction force caused by guides 402 may improve the degree of control a clinician has in implanting IMD 14 and the responsivity of IMD 14 to manipulation of handle 100 and plunger 300, e.g., the ability to control the speed at which IMD 14 is pushed out and to provide a force to stop the motion of IMD 14 in channel 102 when the clinician stops pushing plunger.

In some examples, guides 402 are configured to maintain an orientation and/or position of IMD 14 including absorbable antibacterial layer 16 as plunger 300 pushes IMD 14 including absorbable antibacterial layer 16 out of distal opening 108 and into the patient. For example, guides 402 may be configured to apply a pressure to the sides of IMD 14 as IMD 14 moves along channel 102 to reduce and/or prevent misalignment of IMD 14 as it is subcutaneously implant, e.g., movement of IMD 14 in a lateral direction, such as motion (translation or rotation of IMD 14) having a directional component perpendicular to longitudinal axis 140.

Absorbable antibacterial layer 16 is configured to be compatible with handle 100 and plunger 300, e.g., the implantation tool. For example, absorbable antibacterial layer 16 is configured to not interfere with movement of IMD 14 within channel 102. Absorbable antibacterial layer 16 may be configured to not interfere with guides 402 or contact points 404, or the interaction of plunger 300 with handle 100, e.g., the protrusion of handle 100 and/or the corresponding groove of the lower surface of plunger 300. For example, absorbable antibacterial layer 16 may be configured to not interfere with plunger 300 engaging with channel 102, e.g., the groove of plunger 300 engaging with the protrusion of handle 100.

In the example shown, absorbable antibacterial layer 16 is disposed on a surface of IMD 14 opposite slot 116, e.g., the "top" surface of IMD 14. As such, absorbable antibacterial layer 16 may come into contact with, or rub on portions or surface of IMD 14, but does not come into contact with contact points 404 or the protrusion of handle 100 or groove of plunger 300 when IMD 14 is moving within channel 102. Absorbable antibacterial layer 16 may additionally be disposed on the opposing "bottom" surface of IMD 14, e.g., adjacent slot 116 of handle 100. Similarly, absorbable antibacterial layer 16 so disposed may come into contact with, or rub on, surfaces of IMD 14 (such as the inner surface of the bottom of channel 102) but does not come into contact with contact points 404 or interfere with the protrusion of handle 100 or the groove of plunger 300 when IMD 14 is moving within channel 102. In some examples, absorbable antibacterial layer 16 may be disposed on the opposing sides of IMD 14 that come into contact with contact points 404.

Absorbable antibacterial layer 16 may be configured to slide along contact points 404, e.g., absorbable antibacterial layer 16 may be substantially smooth, have a lower friction surface and/or coating, or the like. In the example shown, absorbable antibacterial layer 16 on the top of IMD 14 has a mesh-type structure. In some examples, absorbable antibacterial layer 16 disposed on one or both sides of IMD 14 which come into contact points 404 may have relatively smoother surface and/or structure, e.g., a finer mesh and/or smoother surface configured to not get caught or be damaged by contact points 404. In some examples, guides 402 may have reduced force, e.g., to cause contact points 404 to apply a reduced force on the sides of IMD 14 and/or absorbable antibacterial layer 16. In some examples, the surface area of contact points 404 may be configured to be compatible with absorbable antibacterial layer 16, e.g., a reduced surface area to reduce friction against absorbable antibacterial layer 16 disposed on the sides of IMD 14. In some examples, the contacting surface of contact points 404 may be configured to be compatible with absorbable antibacterial layer 16, e.g., a curvature and/or surface roughness of contact points 404 may be reduced to provide a smoother contact area between contact points 404 and absorbable antibacterial layer 16.

Figure 9:
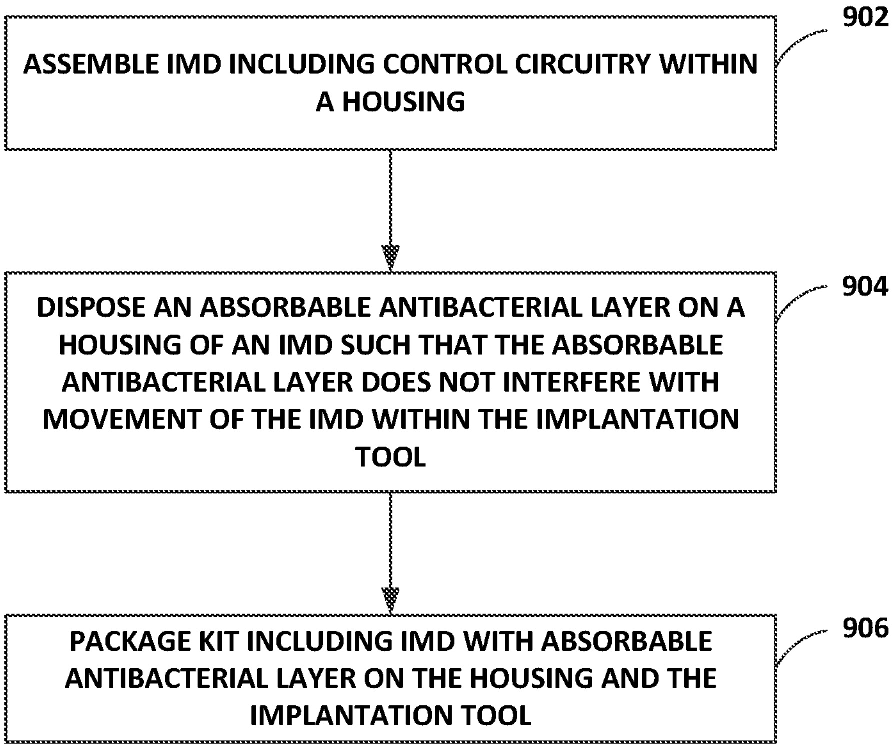
FIG. 9 is a flow diagram of an example method of manufacturing an implantable medical device including an absorbable antibacterial layer, according to various examples described in this disclosure.

FIG. 9 is a flow diagram of an example method of manufacturing an implantable medical device including an absorbable antibacterial layer, according to various examples described in this disclosure. Although the example technique of FIG. 9 is described with respect to medical systems 10, IMD 14, absorbable antibacterial layer 16, handle 100, and plunger 300, of FIGS. 1-8, the example technique of FIG. 9 may be performed using any system including an implantable medical device including an absorbable antibacterial layer described herein. The technique of FIG. 9 may be performed by any suitable user, such as a clinician, and the like.

A manufacturer may assemble an IMD including control circuitry within a housing (902). For example, a manufacturer may assemble IMD 14 including circuitries 36-42 within housing 20. The manufacturer may dispose absorbable antibacterial layer 16 on the housing of IMD 14 such that absorbable antibacterial layer 16 does not interfere with IMD 14 being received within the implantation tool, e.g., channel 102, and being delivered out of the implantation tool and into a patient (904). In some examples, the manufacturer may dispose absorbable antibacterial layer 16 on the housing of IMD 14 by applying an applying an adhesive to the absorbable antibacterial layer, positioning the absorbable antibacterial layer on the housing, applying pressure to adhesive to attach the absorbable antibacterial layer to the housing. In some examples, the manufacturer may dispose absorbable antibacterial layer 16 on at least a portion insulative cover 76 not including an electrode. In some examples, the manufacturer may dispose absorbable antibacterial layer 16 on at least a portion of a surface of the housing of IMD 14 opposing insulative cover 76 and/or a surface of the housing of IMD 14 adjacent to insulative cover 76. The manufacturer may package a kit including IMD 14 with absorbable antibacterial layer 16 on housing 20 with an implantation tool, e.g., an implantation tool including handle 100 and plunger 300 (906).

Figure 10:
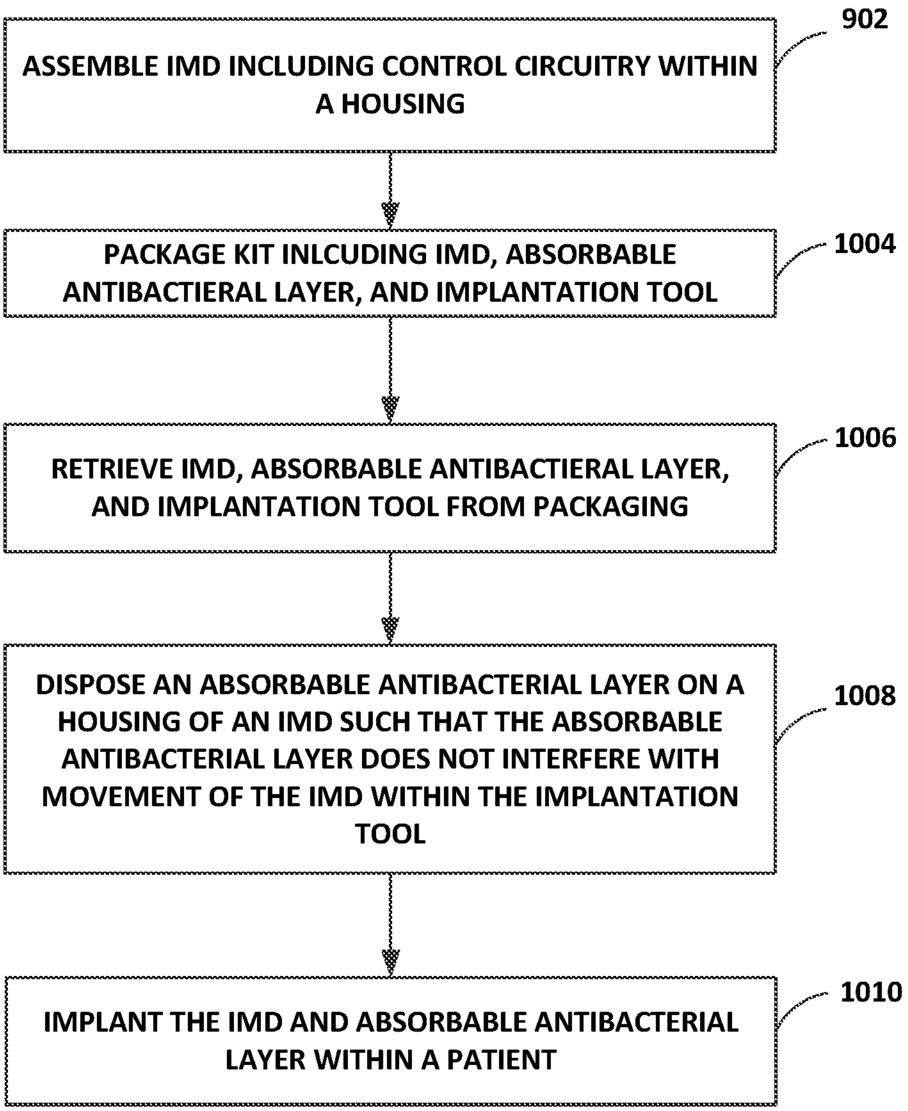
FIG. 10 is a flow diagram of an example method of implanting an implantable medical device including an absorbable antibacterial layer, according to various examples described in this disclosure.

FIG. 10 is a flow diagram of an example method of implanting an implantable medical device including an absorbable antibacterial layer, according to various examples described in this disclosure. Although the example technique of FIG. 9 is described with respect to medical systems 10, IMD 14, absorbable antibacterial layer 16, handle 100, and plunger 300, of FIGS. 1-8, the example technique of FIG. 9 may be performed using any system including an implantable medical device including an absorbable antibacterial layer described herein. The technique of FIG. 9 may be performed by any suitable user, such as a clinician, and the like.

A manufacturer may assemble an IMD including control circuitry within a housing (902), e.g., such as described above. The manufacturer may package a kit including IMD 14, an absorbable antibacterial layer 16, and an implantation tool, e.g., an implantation tool including handle 100 and plunger 300 (1004).

A user and/or clinician may retrieve IMD 14, absorbable antibacterial layer 16, and the implantation tool from the package (1006). The user and/or clinician may dispose absorbable antibacterial layer 16 on the housing of IMD 14 such that absorbable antibacterial layer 16 does not interfere with IMD 14 being received within the implantation tool, e.g., channel 102, and being delivered out of the implantation tool and into a patient (1008). In some examples, the user and/or clinician may dispose absorbable antibacterial layer 16 on the housing of IMD 14 by applying an applying an adhesive to the absorbable antibacterial layer, positioning the absorbable antibacterial layer on the housing, applying pressure to adhesive to attach the absorbable antibacterial layer to the housing. In some examples, the user and/or clinician may dispose absorbable antibacterial layer 16 on at least a portion insulative cover 76 not including an electrode. In some examples, the user and/or clinician may dispose absorbable antibacterial layer 16 on at least a portion of a surface of the housing of IMD 14 opposing insulative cover 76 and/or a surface of the housing of IMD 14 adjacent to insulative cover 76. In some examples, the manufacturer may dispose absorbable antibacterial layer 16 on the housing of IMD 14 such that absorbable antibacterial layer 16 does not interfere with IMD 14 being received within the implantation tool, e.g., per (904) above, and include the IMD14 with the absorbable antibacterial layer 16 on housing 20 and/or insulative cover 76 at step (1004), in which case step (1006) may be omitted.

The user and/or clinician may implant IMD 14 and absorbable antibacterial layer 16 within a patient (1010). For example, the user and/or clinician may position IMD 14 including absorbable antibacterial layer 16 within the implantation tool such that absorbable antibacterial layer 16 does not interfere with movement of IMD 14 within channel 102 of IMD 14. The clinician may then implant IMD 14, e.g., including absorbable antibacterial layer 16, within a patient.

This disclosure includes the following non-limiting examples.

Example 1: An implantable medical device including: a housing configured to house control circuitry, wherein the control circuitry is configured to control functioning of the implantable medical device; an electrode positioned on an outer surface of the housing and connected to the control circuitry, wherein the control circuitry is configured to monitor a physiological parameter of a patient via the electrode; and an absorbable antibacterial layer disposed on the housing, wherein the implantable medical device including the absorbable antibacterial layer is configured to be received within an implantation tool and delivered out of the implantation tool and into a patient.

Example 2: The implantable medical device of example 1, wherein the physiological parameter is a cardiac parameter of the patient.

Example 3: The implantable medical device of example 1 or example 2, wherein the control circuitry is configured to sense electrical signals associated with the electrical activity of the heart or other cardiac tissue of the patient via the electrode.

Example 4: The implantable medical device of any one of examples 1 through 3, wherein the housing comprises a non-metallic portion attached to a metallic portion.

Example 5: The implantable medical device of example 4, wherein the absorbable antibacterial layer is disposed on the non-metallic portion.

Example 6: The implantable medical device of example 4 or example 5, wherein the control circuitry formed on the non-metallic portion and located within the housing of the implantable medical device.

Example 7: The implantable medical device of any one of examples 4 through 6, wherein the electrode is positioned on an outer surface of the non-metallic portion.

Example 8: The implantable medical device of example 7, wherein the absorbable antibacterial layer is disposed on an area of the non-metallic portion not including the electrode.

Example 9: The implantable medical device of example 7 or 8, wherein the electrode comprises a first electrode, the implantable medical device further comprising a second electrode wherein the absorbable antibacterial layer is disposed on an area of the non-metallic portion not including the first electrode or the second electrode.

Example 10: The implantable medical device of any of examples 4 through 9, further comprising an antenna within the housing of the implantable medical device and connected to the non-metallic portion, the antenna connected to the control circuitry and configured to send and receive communication signals, wherein the absorbable antibacterial layer disposed on an area of the non-metallic portion that is not opposite the antenna.

Example 11: The implantable medical device of any one of examples 1 through 3, wherein the absorbable antibacterial layer is disposed on an area of the housing not including the electrode.

Example 12: The implantable medical device of any one of examples 1 through 3 or 11, further comprising an antenna within the housing of the implantable medical device, the antenna connected to the control circuitry and configured to send and receive communication signals, wherein the absorbable antibacterial layer disposed on an area of the housing that is not opposite the antenna.

Example 13: The implantable medical device of any one of examples 1 through 12, wherein the absorbable antibacterial layer disposed on the housing in a pattern, the pattern comprising the absorbable antibacterial layer disposed on a first area of the housing and the absorbable antibacterial layer not disposed on a second area of the housing.

Example 14: The implantable medical device of example 13, wherein the absorbable antibacterial layer is etched into the pattern.

Example 15: The implantable medical device of example 13 or 14, wherein the pattern is configured to not interfere with the efficacy of the electrode receiving a physiological signal.

Example 16: The implantable medical device of any one of examples 1 through 15, wherein the absorbable antibacterial layer is configured to at least one of prevent or reduce growth of bacteria in the patient.

Example 17: The implantable medical device of any one of examples 1 through 16, wherein the absorbable antibacterial layer comprises at least one of rifampin or minocycline.

Example 18: The implantable medical device of any one of examples 1 through 17, wherein the absorbable antibacterial layer is configured to reduce a migration of the implantable medical device when the implantable medical device is implanted within the patient.

Example 19: The implantable medical device of example 18, wherein the absorbable antibacterial layer comprises a surface relief structure configured to reduce the migration of the implantable medical device when the implantable medical device is implanted within the patient.

Example 20: The implantable medical device of any one of examples 1 through 19, wherein the absorbable antibacterial layer is a mesh comprising a plurality of filaments.

Example 21: The implantable medical device of any one of examples 1 through 20, wherein the absorbable antibacterial layer is configured to receive a suture.

Example 22: The implantable medical device of any one of examples 1 through 21, wherein the absorbable antibacterial layer is further configured to release from tissue of the patient upon removal of the implantable medical device from the patient.

Example 23: The implantable medical device of any one of examples 1 through 22, wherein the absorbable antibacterial layer is disposed on the housing via an adhesive.

Example 24: The implantable medical device of any one of examples 1 through 23, wherein the absorbable antibacterial layer is disposed on the housing via a compression fit.

Example 25: The implantable medical device of any one of examples 1 through 24, wherein the absorbable antibacterial layer is disposed on greater than or equal to 20% of the outer surface of the housing.

Example 26: The implantable medical device of any one of examples 1 through 25, wherein the absorbable antibacterial layer is disposed on substantially all of the surface area of the outer surface of the housing that is not the electrode.

Example 27: The implantable medical device of any one of examples 1 through 26, wherein the absorbable antibacterial layer has a thickness from 0.025 millimeters (mm) to 10 mm.

Example 28: The implantable medical device of any one of examples 1 through 27, wherein the absorbable antibacterial layer has a thickness from 1 mm to 5 mm.

Example 29: The implantable medical device of any one of examples 1 through 28, wherein the absorbable antibacterial layer is configured such that between 45% to 55% of an absorbable antibacterial material comprising the absorbable antibacterial layer is absorbed by the patient within 30 to 60 days.

Example 30: The implantable medical device of any one of examples 1 through 28, wherein the absorbable antibacterial layer is configured such that between 65% to 75% of an absorbable antibacterial material comprising the absorbable antibacterial layer is absorbed by the patient after 90 days.

Example 31: A system including: an implantable medical device and an implantation tool including: a tool body defining a longitudinal axis and a channel extending along the longitudinal axis, the channel having a distal opening, wherein the tool body is configured to receive the medical device within the channel; and a plunger slidably fitting within the channel and movable within the channel towards the distal opening, wherein a distal end of the plunger is configured to push a proximal end of the medical device out of the channel through the distal opening, wherein the absorbable antibacterial layer, when disposed on the housing of the implantable medical device, is configured to be compatible with the implantation tool.

Example 32: The system of example 31, wherein the absorbable antibacterial layer is configured to not interfere with movement of the implantable medical device within the channel.

Example 33: The system of example 31 or example 32, wherein the tool body defines a first projection into the channel, wherein the plunger defines a groove that corresponds to and engages with the first projection into the channel, wherein the absorbable antibacterial layer is configured to not interfere with the plunger engaging the channel.

Example 34: The system of example 33, wherein the tool body further comprises: a guide configured to releasably hold the medical device within the implantation tool via a friction fit, wherein the guide is configured to control an orientation of the implantable medical device while the plunger pushes the proximal end of the medical device out of the channel through the distal opening, wherein the absorbable antibacterial layer is configured to not interfere with the guide.

Example 35: A kit including: an implantable medical device and an implantation tool including: a tool body defining a longitudinal axis and a channel extending along the longitudinal axis, the channel having a distal opening, wherein the tool body is configured to receive the medical device within the channel; and a plunger slidably fitting within the channel and movable within the channel towards the distal opening, wherein a distal end of the plunger is configured to push a proximal end of the medical device out of the channel through the distal opening, wherein the absorbable antibacterial layer, when disposed on the housing of the implantable medical device, is configured to be compatible with the implantation tool.

Example 36: The kit of example 35, further comprising a sterile container configured to receive the implantable medical device and implantation tool.

Example 37: The kit of example 36, wherein the absorbable antibacterial layer is separate from the housing and is configured to be disposed on the housing, wherein the absorbable antibacterial layer, the implantable medical device, and the implantation tool are disposed within the sterile container.

Example 38: An article including: a material layer having a first thickness; and an absorbable antibacterial material at least one of disposed on the material layer or disposed within the material layer, the absorbable antibacterial material configured to be absorbed by a patient from the material layer when the article is implanted within the patient, wherein the material layer is configured to be disposed on a housing of an implantable medical device, wherein the material layer, when disposed on the housing, is configured to be compatible with an implantation tool.

Example 39: A method of manufacturing the implantable medical device of any of examples 1 through 30 including: disposing the absorbable antibacterial layer on the housing of the implantable medical device such that the absorbable antibacterial layer does not interfere with the implantable medical device being received within the implantation tool and being delivered out of the implantation tool and into a patient.

Example 40: The method of example 39, wherein disposing the absorbable antibacterial layer on the housing of the medical device comprises: applying an adhesive to the absorbable antibacterial layer; positioning the absorbable antibacterial layer on the housing; and applying pressure to adhesive to attach the absorbable antibacterial layer to the housing.

Example 41: The method of example 39 or example 40, wherein the housing of the implantable medical device includes a first surface including an electrode, wherein the disposing the antibacterial layer on the housing of the implantable device comprises disposing the antibacterial layer on a portion of the first surface not including the electrode.

Example 42: The method of example 41, further comprising marking the absorbable antibacterial layer to be cut to be disposed on the portion of the first surface not including the electrode.

Example 43: The method of example 41, further comprising cutting the absorbable antibacterial layer to a size compatible with the portion of the first surface not including the electrode.

Example 44: The method of example 41, wherein the housing of the implantable medical device includes a second surface opposing the first surface, wherein the disposing the antibacterial layer on the housing of the implantable device comprises disposing the antibacterial layer on at least a portion of the second surface.

Example 45: A method of implanting the implantable medical device of any of examples 1 through 30 including: positioning the implantable medical device within the implantation tool such that the absorbable antibacterial layer does not interfere with movement of the implantable medical device within a channel of the implantable medical device; and implanting, via the implantation tool, the implantable medical device within a patient.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processor circuitry," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random-access memory (RAM), read-only memory (ROM), non-volatile random-access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of this disclosure have been described. These and other aspects are within the scope of the following claims.

What is claimed is:

1. An implantable medical device comprising:

a housing configured to house control circuitry, wherein the control circuitry is configured to control functioning of the implantable medical device;

an electrode positioned on an outer surface of the housing and connected to the control circuitry, wherein the control circuitry is configured to monitor a physiological parameter of a patient via the electrode; and an absorbable antibacterial layer disposed on the housing that is at least one of adhered with an adhesive on or forms a member that is fitted over an area of the housing not including where the electrode is positioned, wherein the implantable medical device including the absorbable antibacterial layer is configured to be received within an implantation tool and delivered out of the implantation tool and into a patient.

2. The implantable medical device of claim 1, wherein the physiological parameter is a cardiac parameter of the patient.

3. The implantable medical device of claim 1, wherein the control circuitry is configured to sense electrical signals associated with the electrical activity of the heart or other cardiac tissue of the patient via the electrode.

4. The implantable medical device of claim 1, wherein the housing comprises a non-metallic portion attached to a metallic portion.

5. The implantable medical device of claim 4, wherein the absorbable antibacterial layer is disposed the at least one of adhered with an adhesive on or forms the member that is fitted over the non-metallic portion.

6. The implantable medical device of claim 4, wherein the control circuitry formed on the non-metallic portion and located within the housing of the implantable medical device.

7. The implantable medical device of claim 4, wherein the electrode is positioned on an outer surface of the non-metallic portion.

8. The implantable medical device of claim 7, wherein the absorbable antibacterial layer is disposed the at least one of adhered with an adhesive on or forms the member that is fitted over an area of the non-metallic portion not including where the electrode is positioned.

9. The implantable medical device of claim 7, wherein the electrode comprises a first electrode, the implantable medical device further comprising a second electrode wherein the absorbable antibacterial layer is disposed the at least one of adhered with an adhesive on or forms the member that is fitted over an area of the non-metallic portion not including where the first electrode or the second electrode are positioned.

10. The implantable medical device of claim 4, further comprising an antenna within the housing of the implantable medical device and connected to the non-metallic portion, the antenna connected to the control circuitry and configured to send and receive communication signals, wherein the absorbable antibacterial layer disposed the at least one of adhered with an adhesive on or forms the member that is fitted over an area of the non-metallic portion that is not opposite the antenna.

11. The implantable medical device of claim 1, further comprising an antenna within the housing of the implantable medical device, the antenna connected to the control circuitry and configured to send and receive communication signals, wherein the absorbable antibacterial layer disposed the at least one of adhered with an adhesive on or forms the member that is fitted over an area of the housing that is not opposite the antenna.

12. The implantable medical device of claim 1, wherein the absorbable antibacterial layer disposed the at least one of adhered with an adhesive on or forms the member that is fitted over the housing in a pattern, the pattern comprising the absorbable antibacterial layer disposed on a first area of the housing and the absorbable antibacterial layer not disposed on a second area of the housing.

13. The implantable medical device of claim 12, wherein the absorbable antibacterial layer is etched into the pattern.

14. The implantable medical device of claim 12, wherein the pattern is configured to not interfere with the efficacy of the electrode receiving a physiological signal.

15. The implantable medical device of claim 1, wherein the absorbable antibacterial layer comprises at least one of rifampin or minocycline.

16. A system comprising:

an implantable medical device comprising a housing and an electrode positioned on an outer surface of the housing;

an absorbable antibacterial layer disposed on a housing of the implantable medical device that is at least one of adhered with an adhesive on or forms a member that is fitted over an area of the housing not including where the electrode is positioned; and an implantation tool comprising:

a tool body defining a longitudinal axis and a channel extending along the longitudinal axis, the channel having a distal opening, wherein the tool body is configured to receive the medical device within the channel; and a plunger slidably fitting within the channel and movable within the channel towards the distal opening, wherein a distal end of the plunger is configured to push a proximal end of the medical device out of the channel through the distal opening, wherein the implantable medical device with the absorbable antibacterial layer disposed on the housing is configured to be compatible with the implantation tool.

17. The system of claim 16, wherein the tool body defines a first projection into the channel, wherein the plunger defines a groove that corresponds to and engages with the first projection into the channel, wherein the absorbable antibacterial layer is configured to not interfere with the plunger engaging the channel.

18. An article comprising:

a material layer having a first thickness; and an absorbable antibacterial material at least one of disposed on the material layer or disposed within the material layer, the absorbable antibacterial material configured to be absorbed by a patient from the material layer when the article is implanted within the patient, wherein the material layer is configured to be disposed on a housing of an implantable medical device at least one of adhered with an adhesive on or forms a member that is fitted over an area of the housing not including where the electrode is positioned, wherein the material layer, when disposed the at least one of adhered with an adhesive on or forming the member that is fitted over the housing, is configured to be compatible with an implantation tool.

19. A method of implanting an implantable medical device, the method comprising:

positioning the implantable medical device within an implantation tool such that an absorbable antibacterial layer does not interfere with movement of the implantable medical device within a channel of the implantation tool; and implanting, via the implantation tool, the implantable medical device within a patient, wherein the implantable medical device comprises:

a housing configured to house control circuitry, wherein the control circuitry is configured to control functioning of the implantable medical device;

an electrode positioned on an outer surface of the housing and connected to the control circuitry, wherein the control circuitry is configured to monitor a physiological parameter of a patient via the electrode; and the absorbable antibacterial layer disposed on the housing that is at least one of adhered with an adhesive on or forms a member that is fitted over an area of the housing not including where the electrode is positioned.

* * * * *